United States Patent [19]
Albert et al.

[11] Patent Number: 4,510,159
[45] Date of Patent: Apr. 9, 1985

[54] (+)-CYANIDAN-3-OL DERIVATIVES, PHARMACEUTICAL PREPARATIONS THAT CONTAIN SUCH COMPOUNDS, AND THE USE OF THE LATTER TO TREAT LIVER OR VENOUS DISEASES

[75] Inventors: Alban I. Albert, Grand-Saconnex; Marc E. Ballenegger, Gimel, both of Switzerland; Jan C. Overeem, Scherpenzaal, Netherlands; Robert G. Tyson, Prestatyn, Wales

[73] Assignee: Zyma SA, Nyon, Switzerland

[21] Appl. No.: 499,644

[22] Filed: May 31, 1983

[30] Foreign Application Priority Data

Jun. 1, 1982 [GB] United Kingdom ............... 8215868

[51] Int. Cl.³ .................. A61K 31/36; A61K 31/35; C07D 311/62
[52] U.S. Cl. ............................ 514/456; 514/893; 549/399; 549/337
[58] Field of Search ............ 549/399, 337; 424/283, 424/282

[56] References Cited

U.S. PATENT DOCUMENTS 4,166,861  9/1979  Bonati et al. ........... 549/399
4,255,336  3/1981  Albert et al. ........... 549/399

FOREIGN PATENT DOCUMENTS 2345441  10/1977  France .

OTHER PUBLICATIONS

Takaoka et al., Bull. Chem. Soc., Japan, vol. 50, No. 10, pp. 2821-2822, (1977).

Primary Examiner—Nicky Chan
Attorney, Agent, or Firm—Michael W. Glynn

[57] ABSTRACT

Compound of the formula in which
R and R' represent hydrogen or an optionally substituted hydrocarbon radical or acyl radical,
$R_1$ represents hydrogen or an optionally substituted hydrocarbon radical of aliphatic or aromatic character,
$R_2$ represents hydrogen or an optionally substituted hydrocarbon radical of higher aliphatic or aromatic character,
it being possible for
$R_1$ and $R_2$ together to represent also an optionally substituted alkylene radical or an optionally substituted biphenyl-2,2'-ylene radical,
whereby however, when R, $R_1$ and $R_2$ are hydrogen, R' cannot be methyl and salts of such compounds that contain a salt-forming grouping, and pharmaceutical compositions containing these compounds.

The pharmaceutical compositions containing these compounds are particularly valuable for treating liver and veneous diseases.

11 Claims, No Drawings

(+)-CYANIDAN-3-OL DERIVATIVES, PHARMACEUTICAL PREPARATIONS THAT CONTAIN SUCH COMPOUNDS, AND THE USE OF THE LATTER TO TREAT LIVER OR VENOUS DISEASES

The invention relates to novel (+)-cyanidan-3-ol derivatives, especially 3',4'-O,O-substituted methylene-(+)-cyanidan-3-ol derivatives, processes for their manufacture, pharmaceutical preparations that contain such compounds, and their use for the manufacture of pharmaceutical preparations or as pharmacologically active compounds.

The invention relates to compounds of the formula

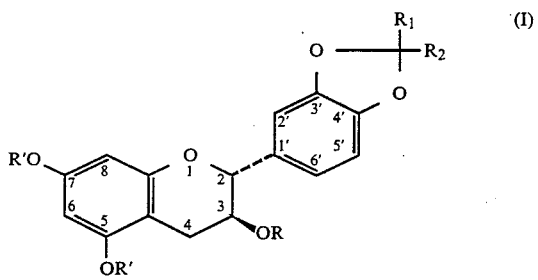

in which
R and R' represent hydrogen or an optionally substituted hydrocarbon radical or acyl radical,
$R_1$ represents hydrogen or an optionally substituted hydrocarbon radical of aliphatic or aromatic character,
$R_2$ represents hydrogen or an optionally substituted hydrocarbon radical of higher aliphatic or aromatic character,
it being possible for
$R_1$ and $R_2$ together to represent also an optionally substituted alkylene radical or an optionally substituted biphenyl-2,2'-ylene radical,
whereby however, when R, $R_1$ and $R_2$ are hydrogen, R' cannot be methyl and salts of such compounds that contain a salt-forming grouping, processes for the manufacture of these compounds, pharmaceutical preparations that contain such compounds, and their use for the manufacture of pharmaceutical preparations or as pharmacologically active compounds.

An optionally substituted hydrocarbon radical denoted by R and R' is, for example, an aliphatic, cycloaliphatic, cycloaliphatic-aliphatic, aromatic, aromatic-aliphatic or heterocyclic-aliphatic radical.

An aliphatic hydrocarbon radical, which may optionally be substituted, is especially an alkyl, alkenyl or alkynyl radical, especially a lower alkyl, lower alkenyl or lower alkynyl radical. Substituents of aliphatic hydrocarbon radicals are, for example, free, esterified or etherified hydroxy groups, free or etherified mercapto groups, such as lower alkanoyloxy, lower alkoxy or lower alkenyloxy groups, lower alkylthio, lower alkylsulphinyl groups, halogen or nitro, and optionally esterified carboxy groups, such as lower alkoxycarbonyl.

Lower alkyl groups are, for example, methyl, ethyl, n-propyl, isopropyl, n-butyl, isobutyl, sec.-butyl, tert.-butyl, n-pentyl, isopentyl, neopentyl, n-hexyl, isohexyl or n-heptyl groups; lower alkenyl groups are, for example, vinyl, allyl, n-propenyl, isopropenyl, 2- or 3-methallyl or 3-butenyl groups, and lower alkynyl groups are, for example, propargyl or 2-butynyl groups. Substituted lower alkyl groups are, for example, nitro-lower alkyl groups, hydroxy-lower alkyl groups, the trifluoromethyl group, hydroxycyano-lower alkyl groups, hydroxyamino-lower alkyl groups, lower alkylthio-lower alkyl groups, the acetyl group or optionally esterified carboxy-lower alkyl groups, such as, for example, a lower alkoxycarbonylethyl group, for example the methoxycarbonylethyl group, an optionally substituted imino-lower alkyl group, such as, for example, an optionally esterified hydroxyimino-lower alkyl group, an alkyl- or optionally substituted phenyl-imino-lower alkyl group, an acetoxyimino-lower alkyl group, an amino-lower alkyl group, a hydroxyamino-lower alkyl group, a di-lower alkylamino-lower alkyl group, or a lower alkyleneamino-lower alkyl group, for example a 1-pyrrolidinyl- or piperidino-lower alkyl group. As a further substituted lower alkyl group there comes into consideration a lower alkyl group substituted by a 2,2-di-lower alkyl-4,6-dioxo-1,3-dioxan-5-ylidene group, such as, for example, [(2,2-dimethyl-4,6-dioxo-1,3-dioxan-5-ylidene)-methyl]. Substituted lower alkenyl groups are, for example, optionally esterified carboxy-lower alkenyl groups, nitro-lower alkenyl groups, methylsulphinyl-lower alkenyl groups, methylsulphonyl-lower alkenyl groups or (acetoxymethylthio)-lower alkenyl groups.

An optionally substituted cycloaliphatic or cycloaliphatic-aliphatic radical is, for example, a mono-, bi- or poly-cyclic cycloalkyl or cycloalkenyl radical or a cycloalkyl- or cycloalkenyl-lower alkyl or -lower alkenyl radical, wherein the cycloalkyl radical contains up to 12, for example from 3 to 8, but especially from 3 to 6, ring carbon atoms, whilst a cycloalkenyl radical has, for example, up to 12, but preferably 5 or 6, carbon atoms and one or two double bonds. The aliphatic moiety of a cycloaliphatic-aliphatic radical can contain up to 7, but preferably up to 4, carbon atoms. The mentioned cyclic radicals can, if desired, be mono-, di- or poly-substituted in analogous manner to the aromatic radicals given hereinbelow.

An optionally substituted aromatic hydrocarbon radical is, for example, a monocyclic, bicyclic or polycyclic aromatic radical, such as the phenyl or naphthyl radical which may be mono-, di- or poly-substituted. These radicals can be substituted preferably by hydroxy, by halogen, such as, for example, bromine or fluorine, or by lower alkyl, such as, for example, methyl, or by lower alkoxy, such as, for example, methoxy, or by a nitro group or by a lower alkoxycarbonyl group, such as, for example, ethoxycarbonyl, or by lower alkanoyloxy, such as, for example, acetoxy or by an optionally substituted amino group, for example the dimethylamino group.

An optionally substituted aromatic-aliphatic hydrocarbon radical is, for example, an aliphatic hydrocarbon radical that carries up to 3 mono-, bi- or poly-cyclic aromatic radicals which may also be substituted. It is especially phenyl-lower alkyl, and also phenyl-lower alkenyl or phenyl-lower alkynyl. These radicals may, if desired, be mono-, di- or poly-substituted in the aromatic or aliphatic moiety, in the manner stated above.

A heterocyclic radical in a heterocyclic-aliphatic group is especially a monocyclic radical. However, it may also be bicyclic or polycyclic, and is especially an aza-, thia-, oxa-, thiaza-, oxaza- or diaza-cyclic radical, which is saturated or unsaturated, for example of aromatic character, and preferably contains from 2 to 7 carbon atoms. These radicals may be mono-, di- or poly-substituted in the cyclic moiety. The aliphatic radicals in a heterocyclic-aliphatic radical may have the meanings given above for the aliphatic moiety of the cycloaliphatic-aliphatic or aromatic-aliphatic radicals.

An optionally substituted hydrocarbon radical $R_1$ of aliphatic or aromatic character corresponds to the definitions of aliphatic or aromatic hydrocarbon radicals given above for R and R'.

An optionally substituted hydrocarbon radical $R_2$ of higher aliphatic or aromatic character is, for example, a higher aliphatic, or homocyclic or heterocyclic aromatic radical.

A higher aliphatic hydrocarbon radical is especially an optionally substituted alkyl or alkenyl radical having at least 9 carbon atoms, especially a higher alkyl or higher alkenyl radical. Substituents of such aliphatic hydrocarbon radicals are, for example, free, esterified or etherified hydroxy groups, free or etherified mercapto groups, such as lower alkanoyloxy, lower alkoxy or lower alkenyloxy groups, lower alkylthio or lower alkylsulphinyl groups, halogen or nitro, and optionally esterified carboxy groups, such as lower alkoxycarbonyl.

Higher alkyl groups are, for example, those having from 9 to 24 carbon atoms, such as decyl, dodecyl, tetradecyl, hexadecyl, octadecyl, eicosyl, docosyl, tetracosyl, but also those having carbon chains that are branched. Higher alkenyl groups are, for example, decenyl etc, and especially octadecenyl. Substituted alkyl groups are, for example, nitroalkyl groups, hydroxyalkyl groups, hydroxycyanoalkyl groups, hydroxyaminoalkyl groups, lower alkylthioalkyl groups, acetylalkyl groups or an optionally esterified carboxyalkyl group, such as, for example, a lower alkoxycarbonyldecyl group, for example a methoxycarbonyldecyl group, an optionally substituted iminoalkyl group, such as, for example, an optionally esterified hydroxyiminoalkyl group, an alkyl- or optionally substituted phenyliminoalkyl group, an acetoxyiminoalkyl group, an aminoalkyl group, a hydroxyaminoalkyl group, a di-lower alkylaminoalkyl group, or a lower alkenylaminoalkyl group, for example a pyrrolidin-1-yl- or piperidinoalkyl group. As a further substituted alkyl group there comes into consideration an alkyl group substituted by a 2,2-di-lower alkyl-4,6-dioxo-1,3-dioxan-5-ylidene group, such as, for example, (2,2-dimethyl-4,6-dioxo-1,3-dioxan-5-ylidene)-methyl. Substituted alkenyl groups are, for example, optionally esterified carboxyalkenyl groups, nitroalkenyl groups, methylsulphinylalkenyl groups, methylsulphonylalkenyl groups or acetoxymethylthioalkenyl groups.

An optionally substituted hydrocarbon radical $R_2$ of aromatic character corresponds to the definitions for aromatic hydrocarbons given above for R and R'.

$R_1$ and $R_2$ can together also represent an optionally substituted alkylene radical that has, for example, from 2 to 7 carbon atoms, such as, for example, the ethylene, propylene, butylene, pentylene, hexylene or heptylene radical. $R_1$ and $R_2$ may represent, for example as an optionally substituted biphenyl-2,2'-ylene radical together with the adjacent carbon atom, the 9,9-fluorenylene radical.

The acyl radicals of an aliphatic carboxylic acid are especially acyl radicals of alkanecarboxylic acids, especially lower alkanecarboxylic acids or lower alkanedicarboxylic acids, such as, for example, succinic acid, and also of alkenecarboxylic acids, especially lower alkenecarboxylic acids or lower alkenedicarboxylic acids, and also substituted lower alkanecarboxylic acids, such as, for example, trifluoroacetic acid.

The acyl radical R' and R'' of cycloaliphatic cycloaliphatic-aliphatic, aromatic and aromatic-aliphatic carboxylic acids have, both in the case of the ring and in the case of the aliphatic moiety which may be present, the meanings given above for the corresponding hydrocarbon radicals. They may also carry substituents, such as, for example, hydroxy, halogen, lower alkyl or lower alkoxy. As aromatic acyl radical there comes into consideration, for example, the benzoyl radical.

The compounds of the pharmaceutical preparations according to the present invention possess valuable pharmacological properties. They show in particular an activity which is of interest in the prevention of necrosis and hepatic fibrosis and in addition inhibit lipoperoxidation. They also possess immunomodulating and anti-inflammatory properties and can inhibit the release of lysosomal enzymes by increasing the stability of lysosomal membranes. They can even influence the vascular permeability and tonus.

They are useful in the treatment of hepatic diseases such as acute hepatites (viral, alcoholic, toxic), steatoses, chronic hepatites and cirrhoses, particularly those of alcoholic origin.

Modification of experimental hepatitis induced by galactosamine, carbon tetrachloride or ethyl alcohol can be demonstrated in rats pre-treated with those compounds, either orally or intraperitoneally in doses ranging from 25 to 200 mg/kg in acute or chronic administration either in preventive or curative therapy. In acute studies, the animals are sacrificed 24 or 48 hours after administration of the toxic agent and hepatic function is measured by the following tests:
BSP clearance
plasma level of bilirubin
plasma level of transaminase
triglyceride level
total hepatic lipids.
in the chronic studies, hepatic collagen level is measured in addition to the above-mentioned parameters.

Thus, for example, the effect on normal or pathalogical metabolism of the hepatocytes of rats kept alive can be demonstrated on isolated rat hepatocytes using the technique of Berry & Friend, [J. Coll. Biol. 43, 506–520 (1969)] by incubating them in 2 ml Krebs-Ringer physiological solution in the presence of one of the compounds in quantities ranging from 0.1 to 1 mg/ml and with the addition of different hepatotoxic substances. On the other hand, the inhibition of lipoperoxidation by carbon tetrachloride can be demonstrated using the method of Comporti, Sacconi and Danzani, [Enzymologia, 28, 185–203 (1965)], and the intensity of lipoperoxidation in the presence of these new substances in concentrations varying between 5 and 50 μg per 4 ml is measured by quantifying the amount of malonic dialdehyde formed.

These compounds are also useful in the treatment of diseases involving an alteration of the organism's immunological response, such as all recurrent or prolonged viral infections: as, for example, hepatites due to both virus B and non-A-non-B, or recurrent herpes or for the treatment of diseases in which a stimulation of the organism's defence mechanisms may bring about healing or improvement of the patient's condition.

This is particularly the case in viral, bacterial or parasitic infections, cancerous disorders and the entire group of autoimmune diseases such as, for example, rheumatoid polyarthritis.

Immunomodulating properties of these compounds are demonstrated not only in neoplastic models but also by means of current immunological studies. Thus, the detection of these valuable immunomodulating properties is possible by using the leukaemia L1210 Ha model in three types of experiments in mice. For example, isogenous CD2F1 mice are treated on day 0 with $10^7$ irradiated L1210 Ha cells and inoculated on day 14 with varying amounts of living cells possessing the same isogenous leukaemia. The effect of these compounds, which are administered before and after inoculation, is demonstrated by an increased life span and a higher number of survivors on day 30. In addition, CD2F1 mice are inoculated with $10^5$ L1210 Ha cells and injected the following day with $10^7$ irradiated tumour cells. The compounds in question are administered before and after inoculation. The effect of these compounds, administered as above, is highly positive, as they increase both the length of life and the number of survivors at 60 days. Also, additional effects in animals previously immunodepressed by doses of 150 mg of cyclophosphamide per kg confirm these results because they show that the animals' reactivity was intact. Finally CD2F1 mice transplanted with $10^5$ L1210 Ha cells, then treated the following day with Adriamycin, provide the same evidence of the beneficial effects of these compounds, when they are administered at an oral daily dosage of 20 to 1000 mg/kg, more precisely between 100 and 300 mg/kg, for any warm-blooded animal of an average weight of 70 kg.

These compounds possess a beneficial effect not only on ascitic tumours and on leukaemia, but also on a solid tumour, i.e. the Lewis Lung (3LL) carcinoma of mice. As a matter of fact, this neoplastic model is considered by E.O.R.T.C. as that which most closely resembles human tumours. The compounds show positive results in significant manner in three series of studies. The compounds are administered for 10 days to C57 BL/6 mice infected with isogenous tumour 3LL. They are also given after treatment with methyl CCNU (methyl lomustine) in a dose of 10 mg/kg to animals with tumour. They act also by limiting the development of metastases when the primary tumour has been removed surgically.

These compounds possess also immunostimulating activity. Thus their pharmaceutical potential has been proved in in vivo studies by showing their ability to increase the cytotoxic capacity of purified macrophages towards cancerous cells. In fact, these macrophages, whose capacities have been appreciably increased by these substances, are believed to play an important role in both antitumoral resistance and control of immunological reactivity.

These compounds also have clearly demonstrated their therapeutic potential by showing without any possibility of doubt their positive effect on antibody production in non-neoplastic conditions which in fact proves that their effect is in fact due to the host's reactivity. When CD2F1 mice are injected with $10^8$ sheep erythrocytes (SRBC) or with 0.5 μg polysaccharide of pneumococci S. III, the number of spleen cells capable of producing specific antibodies is significantly increased as can be shown in the haemolytic plaque assay according to Jerne & Nordin. The antibodies are measured by peak responses either after single or repeated injections of one of these compounds.

Finally, as these compounds stabilize lysosomal membranes, potentiate the cytotoxic capacity of macrophages and decrease vascular permeability, they are useful for the treatment of disease states such as acute and chronic bronchitis in which the existing pathology of hypersecretion is complicated both by chronic inflammatory reactions and recurrent infections.

These compounds are also useful for the treatment of venous or arterial circulatory diseases.

The anti-inflammatory, vasculotropic and protective properties of the compounds towards the connective tissue may be demonstrated in the following studies:

(1) At doses varying between 100 and 500 mg/kg, by parenteral or oral administration, they are able to reduce oedema caused by galactosamine, by heat and by stasis. Even more important, these beneficial effects are seen in the absence of any central haemodynamic activity. The compounds favourably modify vascular reactivity in terms of both micro- and macro-circulation. They are also capable of improving peripheral blood circulation (legs). Finally, these substances counteract the toxic effects of histamine in cultures of endothelial cells.

Pharmacological activities of 3',4'-O,O-methylene-substituted derivatives of (+)-cyanidan-3-ol on venous disease model: D-galactosamine oedema.

Results are expressed in percentage inhibition of the oedema related to a non-treated standard intoxicated in the same way as the treated animal. Dose is indicated in mg/kg and mode of administration is intraperitoneal (i.p.).

| substance | dose | % inhibition |
| --- | --- | --- |
| 3',4'-O,O—diphenylmethylene-(+)-cyanidan-3-ol | 50 mg/kg | 31.6% |
| 3',4'-O,O—[di-(4''-fluoro-phenyl)-methylene]-(+)-cyanidan-3-ol | 50 mg/kg | 22.1% |

(2) "In vitro" measurement of both the inhibition of the activity of lysosomal enzymes and the increase of the stability of lysosomal membranes at 0.05 to 2 mg per ml according to P. Niebes & Ponard (Biochem. Pharmacol. 24, 905 (1975)).

(3) "In vitro" measurement of the inhibition of other acute phase reactants, such as kinins, prostaglandins and thromboxanes.

Preferred novel compounds are those of the formula I in which R and R' represent hydrogen, an optionally substituted aliphatic, cycloaliphatic, cycloaliphatic-aliphatic, aromatic or aromatic-aliphatic radical or an acyl radical of an aliphatic or aromatic carboxylic acid, $R_1$ represents hydrogen or an optionally substituted aliphatic or homocyclic or heterocyclic aromatic radical, and $R_2$ represents hydrogen or an optionally substituted higher aliphatic or homocyclic or heterocyclic aromatic radical, it also being possible for $R_1$ and $R_2$ together to represent an optionally substituted alkylene radical or a biphenyl-2,2'-ylene radical as for example fluorene-9,9-ylidene, whereby however, when R, $R_1$ and $R_2$ are hydrogen, R' cannot be methyl, and therapeutically acceptable salts of these compounds.

Especially preferred novel compounds are those of the formula I in which R and R' represent hydrogen, an optionally substituted alkyl, alkenyl or alkynyl radical, an optionally substituted cycloalkyl or cycloalkenyl radical, or a cycloalkyl- or cycloalkenyl-lower alkyl or -lower alkenyl radical or an optionally substituted mono-, bi- or poly-cyclic aryl or aryl-lower alkyl radical or aroyl, $R_1$ represents hydrogen or an optionally substituted alkyl, alkenyl or alkynyl radical, or an optionally substituted phenyl radical, and $R_2$ represents hydrogen, an optionally substituted alkyl or alkenyl radical having at least 9 carbon atoms, or an optionally substituted phenyl radical, it also being possible for $R_1$ and $R_2$ together to represent an optionally substituted alkylene radical or a biphenyl-2,2′-ylene radical, whereby however, when R, $R_1$ and $R_2$ are hydrogen, R′ cannot be methyl, and therapeutically acceptable salts of these compounds.

More especially preferred novel compounds are those of the formula I in which R and R′ represent hydrogen, an alkyl radical optionally substituted by hydroxy, oxo, amino, imino, di-lower alkylamino, halogen, hydroxyimino, phenylimino, nitrophenylimino, acetylimino, cyano, carboxy or by lower alkylsulphinyl, an alkenyl radical optionally substituted by carboxy, lower alkylcarboxy, nitro, methylsulphinyl or by acetoxymethylthio, or an alkynyl radical, a cycloalkyl- or cycloalkenyl-lower alkyl or -lower alkenyl radical, a phenyl or phenyl-lower alkyl radical optionally substituted by halogen, such as, for example, bromine or fluorine, or by lower alkyl, such as, for example, methyl, or by lower alkoxy, such as, for example, methoxy, or by a nitro group or by a di-lower alkylamino group, or benzoyl, $R_1$ represents hydrogen or lower alkyl, lower alkenyl, lower alkynyl, or phenyl optionally substituted by halogen, nitro, lower alkoxy, or by lower alkanoyloxy, and $R_2$ represents hydrogen, alkyl or alkenyl, such a radical containing at least 9 carbon atoms, or phenyl optionally substituted by halogen, nitro, lower alkoxy, or by lower alkanoyloxy, it also being possible for $R_1$ and $R_2$ together to represent an optionally substituted alkylene radical or a biphenyl-2,2′-ylene radical, whereby however, when R, $R_1$ and $R_2$ are hydrogen, R′ cannot be methyl 2,2′-ylene radical, and therapeutically acceptable salts of these compounds.

The novel compounds specifically preferred are those of the formula I in which R and R′ represent hydrogen or lower alkylbenzyl, and $R_1$ and $R_2$ represent phenyl optionally substituted by halogen, nitro, lower alkoxy or by lower alkanoyloxy, and therapeutically acceptable salts of these compounds.

The compounds most especially preferred are:
3′,4′-O,O-(diphenylmethylene)-(+)-cyanidan-3-ol.
3′,4-O,O[di-(4″-fluorophenyl)-methylene]-(+)-cyanidan-3-ol
3-(3-carboxypropionyl)-3′,4′-O,O-(diphenylmethylene)-(+)-cyanidan-3-ol sodium salt.

Compounds of the general formula I can be prepared in a manner known per se.

Thus compounds of the formula I may be prepared, for example, by reacting (+)-cyanidan-3-ol or a derivative thereof of the formula II

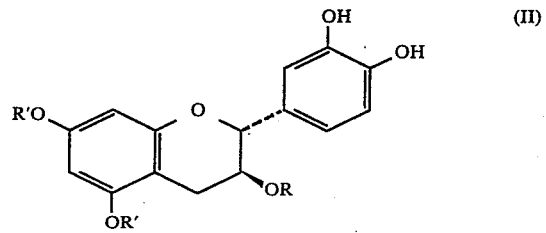

in which R and R′ have the meanings given under formula I, with an oxo compound of the formula III

preferably in the presence of an acid as catalyst.

As catalysts there may be used acids according to Bronsted, that is to say, substances that liberate protons, for example hydrochloric acid, sulphuric acid, calcium chloride, iron(III) chloride, zinc chloride, pyridine hydrochloride and sodium bisulphate. It is also possible to use organic acids, such as, for example, p-toluene-sulphonic acid.

Compounds of the formula I may be prepared according to a further process by reacting (+)-cyanidan-3-ol or a (+)-cyanidan-3-ol derivative of the formula IIa

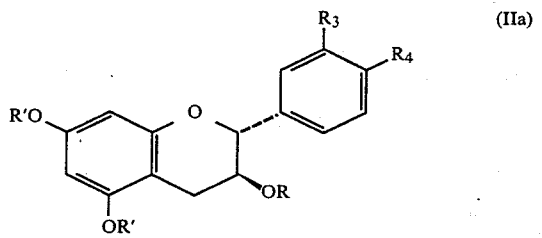

in which $R_3$ and/or $R_4$ represents a hydroxy group that is free, metallated or esterified by a hydrohalic acid, with a compound of the formula IV

in which each of $X_1$ and $X_2$, independently of the other, represents a free, metallated or reactively esterified hydroxy group, but $X_1$ and/or $X_2$ cannot represent a reactively esterified hydroxy group if $R_3$ and/or $R_4$ represent a hydroxy group esterified by a hydrohalic acid.

If $R_3$ and/or $R_4$ are present as a free or metallated hydroxy group, preferably as a hydroxy group metallated by a heavy metal atom, such as, for example, a copper atom, or by an alkali or alkaline earth metal atom, such as, for example a sodium or magnesium atom, $X_1$ and/or $X_2$ are present, for example, in the form of a reactive esterified hydroxy group. Conversely, if $X_1$ and/or $X_2$ are present as free or metallated hydroxy groups, $R_3$ and/or $R_4$ may be present as a halide group.

A reactive esterified hydroxy group $X_1$ and/or $X_2$ is preferably a hydroxy group esterified by a strong mineral or sulphonic acid, such as a hydrohalic, sulphuric, lower alkanesulphonic or benzenesulphonic acid, for example hydrochloric, hydrobromic, methanesulphonic, trifluoromethanesulphonic, benzenesulphonic or p-toluenesulphonic acid. Such esters are, inter alia, lower alkyl halides, di-lower alkyl sulphates, such as dimethyl sulphate, also fluorosulphonic acid esters, such as lower alkyl esters, for example fluorosulphonic acid methyl esters, or optionally halo-substituted methane-sulphonic acid lower alkyl esters, for example trifluoromethanesulphonic acid methyl ester.

The hydroxy groups in the starting material of the formula IV can, however, alternatively be esterified, for example, by a lower alkanoic acid, such as acetic acid or propionic acid. If one of the groups $R_3$ and/or $R_4$ in the compounds of the formula IIa, or $X_1$ and $X_2$ in the compounds of formula IV represent a free hydroxy group, the etherification is carried out in the presence of basic condensation agents that bind the acids formed. Such agents are alkaline earth or alkali metal carbonates or bicarbonates, or tertiary amines, for example tri-lower alkyl amines, or heterocyclic tertiaryamines, or secondary amines, for example di-lower alkylamines, pyridines or lower alkylated pyridines. If one or other of the starting materials of the formula IIa and IV is used in the form of the metallated compound (for example $R_3$ and/or $R_4$ or $X_1$ and $X_2$=ONa), the operation is carried out under neutral reaction conditions. If, finally, $X_1$ and $X_2$ are present in the form of a hydroxy group esterified by a lower alkanoic acid, for example a hydroxy group esterified by acetic acid, the reaction, with a corresponding alcohol, of the compound of the formula II in which $R_3$ and $R_4$ represent a free hydroxy group can be carried out in an acidic medium, preferably in the presence of a mineral acid, for example a hydrohalic acid, for example hydrochloric acid.

The reactions are carried out, if necessary, with the addition of an inert solvent, such as an optionally halogenated, such as chlorinated, aliphatic, cycloaliphatic or aromatic hydrocarbon, for example methylene chloride, an ether, such as dioxan or tetrahydrofuran, a nitrile, for example acetonitrile, an alcohol, for example isopropylalcohol, an amine, for example pyridine, or a mixture of these solvents.

The etherification reaction described above can be considerably accelerated by phase transfer catalysis [see Dehmlow, Angewandte Chemie, Vol. 5, page 187 (1974)]. As phase transfer catalysts there may be used quaternary phosphonium salts and especially quaternary ammonium salts, such as optionally substituted tetraalkylammonium halides, for example tetrabutylammonium chloride, bromide or iodide, or benzyltriethylammonium chloride, in catalytic or up to equimolar amounts. As organic phases there may be used any water-immiscible solvent, for example one of the optionally halogenated, such as chlorinated, lower aliphatic, cycloaliphatic or aromatic hydrocarbons, such as trichloroethylene or tetrachloroethylene, tetrachloroethane, carbon tetrachloride, chlorobenzene, toluene or xylene. Suitable condensation agents are alkali metal carbonates or bicarbonates, for example potassium or sodium carbonate or bicarbonate, alkali metal phosphates, for example potassium phosphate, and alkali metal hydroxides, for example sodium hydroxide.

Resulting compounds of the formula I in which one of the symbols OR or OR' represents a free hydroxy group can be esterified in analogous manner to the previous process, by reacting a compound of the formula I in which at least one of the above-mentioned symbols represents a free or metallated hydroxy group with a compound of the formula $$X_3-R'' \qquad (V)$$

in which $X_3$ represents a free, metallated or reactively esterified hydroxy group and R" together with the oxygen atom represents at least one of the above-defined ether groups OR' or OR, or $X_3$—R" represents a compound that introduces the ether radical R", wherein at least one of the symbols OR or OR' represents a hydroxy group.

If at least one of the symbols OR' and OR represents a free hydroxy group, further etherifying agents are corresponding tri-substituted oxonium salts (so-called Meerwein salts) or di-substituted carbenium or halonium salts, in which the substituents are the etherifying radicals R, for example tri-lower alkyloxonium salts, and di-lower alkoxycarbenium or di-lower alkoxyhalonium salts, especially the corresponding salts with complex fluorine-containing acids, such as the corresponding tetrafluoroborates, hexafluorophosphates, hexafluorantimonates or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are used preferably in an inert solvent, such as an ether or a halogenated hydrocarbon, for example diethyl ether, tetrahydrofuran or methylene chloride, or in a mixture thereof, if necessary in the presence of a base, such as an organic base, for example a, preferably sterically hindered, tri-lower alkylamine, for example N,N-diisopropyl-N-ethylamine, and while cooling, at room temperature or while gently heating, for example at from approximately $-20°$ C. to approximately $50°$ C., if necessary in a closed vessel and/or in an inert gas atmosphere, for example a nitrogen atmosphere.

If one of the substituents OR or OR' in the compound of the formula I is a free hydroxy group, then, finally, further etherifying agents are corresponding 1-substituted 3-aryltriazene compounds, in which the substituent represents the etherifying radical R and aryl preferably represents optionally substituted phenyl, for example lower alkylphenyl, such as 4-methylphenyl. Such triazene compounds are 3-aryl-1-lower alkyltriazenes, for example 3-(4-methylphenyl)-1-methyltriazene, 3-(4-methylphenyl)-1-ethyltriazene or 3-(4-methylphenyl)-1-isopropyltriazene. These reagents are customarily used in the presence of inert solvents, such as optionally halogenated hydrocarbons or ethers, for example benzene, or solvent mixtures, and while cooling, at room temperature or, preferably, at elevated temperature, for example at from approximately $20°$ C. to approximately $100°$ C., if necessary in a closed vessel and/or in an inert gas atmosphere, for example a nitrogen atmosphere.

Compounds of the general formula I in which at least one of the symbols OR and OR' represents acyloxy, can, however, also be obtained by in a compound of the formula I in which at least one of the symbols OR and OR' represents a free hydroxy group, converting this group into an acyloxy group with an acylating agent that introduces the desired acyl radical of an organic carboxylic acid. Such agents are, for example, corresponding carboxylic acids or functional derivatives thereof, such as anhydrides or acid halides, for example chlorides or bromides. The reactions can optionally be carried out in the presence of condensation agents, in the case of free carboxylic acids, for example in the presence of carbodiimide compounds, such as dicyclohexyl carbodiimide, or carbonyl compounds, such as diimidazolylcarbonyl. When using acid derivatives, for example acid halides, the operation is advantageously carried out in the presence of a basic agent, for example a tri-lower alkylamine, such as triethylamine, or a heterocyclic base, for example pyridine.

Compounds of the general formula I in which at least one of the symbols R and R' represents hydrogen and the remaining symbols have the meanings given under formula I above may also be obtained by, in a compound of the general formula I in which at least one of the symbols OR and OR' represents an ether group that can readily be solvolysed or removed by reduction or, especially, hydrogenolysed, or an acyloxy group that can readily be solvolysed or alternatively hydrogenolysed, and the remaining symbols have the meanings given for OR or OR' under formula I, carrying out solvolysis or reduction or, especially, hydrogenolysis.

An ether group or acyloxy group that can readily be solvolysed or hydrogenolysed is, for example, an ether group or acyloxy group that can be removed by solvolysis, including hydrolysis, acidolysis or alcoholysis, or by means of reduction, including hydrogenolysis.

An acyloxy group that can be removed by solvolysis is, for example, an acyloxy group in which the acyl moiety can be the radical of an organic carboxylic acid, for example lower alkanoyl, such as acetyl, halo-lower alkanoyl, such as haloacetyl, for example chloroacetyl, or carbamoyl, or aroyl, such as benzoyl; the acyl moiety can also be the radical of a semiester of carbonic acid, such as lower alkoxycarbonyl, for example methoxycarbonyl, ethoxycarbonyl or tert.-butoxycarbonyl, 2-halolower alkoxycarbonyl, for example 2,2,2-trichloroethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, and also an optionally substituted 1-polyphenyl-lower alkyl group in which substituents of the phenyl moiety can be, for example, lower alkyl or lower alkoxy, for example methyl or methoxy, and especially trityl, or an organosilyl radical, especially trimethylsilyl.

An ether group that can be removed by solvolysis is, for example, lower alkoxy, for example methoxy or ethoxy, or a 1-phenyl-lower alkoxy group, such as, for example, benzyloxy. These radicals can be substituted by lower alkoxy, for example methoxy or ethoxy, or by lower alkoxyethoxy, for example methoxyethoxy.

Benzyloxy radicals as removable ether groups may optionally be substituted by one or more substituents, such as, for example, lower alkyl, for example methyl, ethyl, isopropyl or n-propyl, halogen, for example chlorine or bromine, or by lower alkoxy, such as, for example, methoxy or ethoxy. These substituents are preferably in the ortho or in the para position.

Likewise removable by solvolysis, especially hydrolysis or alcoholysis, in an acidic medium are aliphatic ether groups that, for their part, are substituted in the α-position by an ether group: such as ethoxymethoxy, butoxymethoxy or 1-ethoxyethoxy, and especially analogous cyclic radicals, for example 1-oxocycloalkan-2-yloxy groups, especially tetrahydropyran-2-yloxy, and also, for example, 4-methoxytetrahydropyran-4-yloxy.

If the solvolysis of the ether or acyloxy groups is effected by hydrolysis, this is carried out, depending on the nature of the removable groups, in the presence of an organic acid, such as p-toluenesulphonic acid, or a mineral acid, such as hydrochloric or sulphuric acid, or an alkali metal or alkaline earth metal hydroxide or carbonate, or in the presence of ammonia or an amine, such as isopropylamine, or hydrazine hydrate. If the solvolysis is carried out by means of one of the above-mentioned acids in an alcohol, for example by means of p-toluenesulphonic acid in ethyl alcohol, the solvolysis is effected by alcoholysis.

Ether groups, such as, for example, lower alkoxy groups, especially methoxy or ethoxy, can be removed in solution or in a melt by means of a metal halide, such as, for example, an aluminium or boron halide, for example aluminium chloride, aluminium tribromide, boron trichloride or boron tribromide. As solvent there are suitable, for example, benzene, nitrobenzene or ethylene chloride. [cf Jour. Chem. Soc. (1961), 1008; Ber. (1943), 76B 900; Journ. Org. Chem. (1962), 27, 2037; Ber. (1960), 93, 2761; Jour. Am. Che. Soc. (1968), 24, 2289; Tetr. Lett. (1966), 4155].

Removable by acidolysis are acyloxy groups in which the acyl moiety represents an acyl radical of a semiester of carbonic acid, such as, for example, tert.-lower alkoxycarbonyl or optionally substituted diphenylmethoxycarbonyl. It is also possible to remove ether groups, such as, for example, tert.-lower alkoxy groups, by acidolysis. Removal by acidolysis can be effected by treatment with suitable strong organic carboxylic acids, such as lower alkanecarboxylic acids optionally substituted by halogen, especially fluorine, especially trifluoroacetic acid (if necessary in the presence of an activating agent, such as anisole), or with formic acid. Where not already mentioned hereinbefore, the above reactions are carried out in the presence of a solvent or solvent mixture, it being possible for suitable reactants to act simultaneously as such.

An ether group that can be removed by reduction, especially by hydrogenolysis, is especially an α-aryl-lower alkyl group, such as an optionally substituted 1-phenyl-lower alkyl group, in which lower alkyl has up to 7 carbon atoms and in which substituents, especially of the phenyl moiety, may be, for example, lower alkyl or lower alkoxy, each having up to 7 carbon atoms, for example methyl or methoxy, but more especially benzyl.

The reductive removal of ether groups OR and OR' may be effected especially, for example, by treatment with catalytically activated hydrogen, such as hydrogen in the presence of a suitable hydrogenation catalyst, for example a nickel, platinum or palladium catalyst, or also a rhodium or ruthenium catalyst, or the operation is carried out with a hydride reducing agent, such as, for example, lithium aluminium hydride.

By acyloxy radicals that can be removed by reduction there are to be understood those groups which are removed by treatment with a chemical reducing agent, (especially with a reducing metal or a reducing metal compound). Such radicals are especially 2-halo-lower alkoxycarbonyloxy, such as 2,2,2-trichloroethoxycarbonyloxy, which are removed, for example, with a reducing heavy metal, such as, for example, zinc, or with a reducing heavy metal salt, such as a chromium-(II) salt, for example a chloride or acetate, customarily in the presence of an organic carboxylic acid, such as formic acid or acetic acid.

The above reduction reactions are carried out in a manner known per se, customarily in the presence of an inert solvent, and, if necessary, while cooling or heating, for example in a temperature range of from approximately −20° to approximately 150°, and/or in a closed vessel under pressure.

Depending upon the ether or acyloxy group present it is preferable to select the mildest of the solvolysis or hydrogenolysis methods described in order to avoid modifications of the flavanol structure and/or solvolysis or hydrogenolysis of the unsubstituted or substituted methylenedioxo group.

In resulting compounds, substituents may be changed within the scope of the definition of the end products. Thus, in a product of the formula I a substituent OR or OR' may be exchanged for a different substituent OR'' by treatment with a different alcohol of the formula R''—OH, in which R'' has the meaning given above, optionally in the presence of an acid. Thus, for example, a lower alkoxy group may be converted into a different lower alkoxy group in known manner, for example by reaction with a diazo-lower alkane or by reaction with a lower alkyl halide, such as an iodide or bromide, for example in the presence of silver oxide or silver carbonate.

The reactions mentioned above are carried out according to methods known per se, in the presence or absence of diluents, preferably those diluents which are inert towards the reactants and dissolve these, catalysts, condensation or neutralisation agents, and/or in an inert atmosphere, while cooling, at room temperature or at elevated temperatures, preferably at the boiling point of the solvent used, at normal or elevated pressure.

Starting compounds of the general formula II are known and are described, for example, in European Patent Application No. 3274.

Starting compounds of the formula III are also known or can be obtained according to known processes, for example according to Friedel-Crafts, by acylation of a hydrocarbon of the formula $R_1H$ with an acid halide of the formula

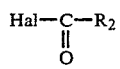

in which Hal represents halogen, especially chlorine or bromine. Some of the starting compounds of the formula IV are also known and may be prepared, for example, from the compounds of the formula III. Thus, for example, compounds of the formula IV in which each of $X_1$ and $X_2$ represents chlorine or bromine, are obtained from the corresponding ketones of the formula III or hydrates thereof with phosphorus pentachloride or phosphorus pentabromide, preferably in a solvent that is inert towards the latter, such as, for example, tetrachloromethane, benzene or petroleum ether, and, if necessary, while heating, for example boiling. Especially compounds of the formula IV in which $X_1$ and $X_2$ represent bromine, but also some of the compounds in which $X_1$ and $X_2$ represent chlorine, may be prepared from the corresponding compounds in which there is hydrogen in place of $X_1$ and $X_2$, by the action of bromine or chlorine, preferably under exposure to light at elevated temperature in an inert solvent, such as tetrachloromethane.

Acid addition salts of compounds of the formula I are obtained in customary manner, for example by treating with an acid or a suitable anion exchanger. The resulting salts can be converted into the free compounds in a manner known per se, for example by treating with a suitable basic agent, for example a metal hydroxide, ammonia or a hydroxyl ion exchanger. On the other hand, compounds having a phenolic hydroxy group can be converted into an alkali metal salt in a manner known per se by treating, for example, with an alkali metal hydroxide. The free compounds can be obtained by treating with an acid.

The therapeutically acceptable salts mentioned above are preferred. These or other salts, for example the picrates, can also be used in the purification of free bases. The bases are converted into their salts, the salts are separated and the bases are liberated from the salts. Owing to the close relationships between the novel compounds in free form and in the form of their salts, hereinbefore and hereinafter there shall optionally be understood by free compounds and salts, where appropriate with regard to meaning and purpose, also the corresponding salts and free compounds, respectively.

Starting materials and end products that are isomeric mixtures can be separated into the individual isomers by methods known per se, for example by fractional distillation, crystallisation and/or chromatography. Racemic products can be separated into the optical antipodes, for example by chromatography and/or separation of their diastereoisomeric salts, for example by fractional crystallisation of the d- or l-camphor-sulphonates, -mandelates, -tartrates or -dibenzoyl-tartrates.

The invention relates also to modifications of the present process, according to which an intermediate obtainable at any stage of the process is used as starting material and the remaining process steps are carried out, or the process is discontinued at any stage, or according to which a starting material is formed under the reaction conditions, or in which a starting material is used in the form of a salt or a reactive derivative. The invention also comprises novel intermediates resulting therefrom.

In the process of the present invention the starting materials used are preferably those which result in the compounds described at the beginning as being especially valuable.

The starting materials used in the process for the manufacture of the compounds of the present invention are known or, if they are novel, they can be manufactured by methods known per se, for example in a manner analogous to that described in the Examples. The invention relates also to novel starting materials.

The pharmaceutical preparations according to the invention contain at least one compound of the general formula I or a salt thereof as the active substance together with a customary pharmaceutical carrier. The type of carrier depends largely on the field of use. The pharmaceutical compositions according to the invention which contain, as active substances, compounds of the formula I can be administered orally, parenterally or rectally.

For oral treatment there come into consideration, especially, solid unit dosage forms, such as tablets, dragées and capsules, which preferably contain between 10 and 90% of an active substance of the general formula I or a salt in order to allow administration to warm-blooded animals of daily doses of from 1 to 50 mg/kg. For the manufacture of tablets and dragée cores, the compounds of the general formula I are combined with solid, pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of a suitable molecular weight. Dragée cores are subsequently coated, for example with concentrated sugar solutions which may contain, in addition, gum arabic, talc and/or titanium dioxide, or with a lacquer dissolved in readily volatile organic solvents or solvent mixtures. Colouring substances can be added to these coatings, for example for indicating different doses of active substance. Soft gelatine capsules and other closed capsules consist, for example, of a mixture of gelatine and glycerin and may contain, for example, mixtures of a compound of the formula I and polyethylene glycol. Dry-filled capsules contain, for example, granules of an active substance with solid, pulverulent carriers, such as, for example, lactose, saccharose, sorbitol, mannitol; starches, such as potato starch, maize starch or amylopectin, cellulose derivatives and gelatine and also magnesium stearate or stearic acid.

Unit dosage forms that come into consideration for rectal administration are, for example, suppositories which consist of a combination of an active substance with a suppository base based on natural or synthetic triglycerides (for example cocoa butter), polyethylene glycols or suitable higher fatty alcohols, and gelatine rectal capsules which contain a combination of the active substance with polyethylene glycols.

Ampoule solutions for parenteral administration, especially for intramuscular or intravenous administration, contain a compound of the formula I or a salt thereof in a concentration of preferably 0.5 to 5% as an aqueous dispersion prepared with the aid of customary solubilisers and/or emulsifiers, and, optionally, stabilisers, or preferably as an aqueous solution of a pharmaceutically acceptable water-soluble salt of a compound of the general formula I.

The concentration of the active substance for liquids that are to be taken orally, such as syrups or elixirs, is so selected that a single dose can easily be measured, for example as the contents of a teaspoon or a measuring spoon of, for example, 5 ml, or also as a multiple of that volume.

The following Examples (a) to (c) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches for a finer adjustment of the dosage.

(b) A granulate is prepared from 100 g of active substance, 379 g of lactose and the alcoholic solution of 6 g of gelatine, and, after being dried, is mixed with 10 g of colloidal silica, 40 g of talc, 60 g of potato starch and 5 g of magnesium stearate and pressed to form 10,000 dragée cores. These are subsequently coated with a concentrated syrup consisting of 533.5 g of crystalline saccharose, 20 g of shellac, 75 g of gum arabic, 250 g of talc, 20 g of colloidal silica and 1.5 g of colouring substance, and dried. The resulting dragées each weigh 150 mg and each contain 10 mg of active substance.

(c) 25 g of active substance and 1975 g of finely ground suppository base (for example, cocoa butter) are thoroughly mixed and then melted. 1000 suppositories of 2 g are cast from the melt which has been kept homogeneous by stirring. They each contain 25 mg of active substance.

The following Examples serve to illustrate the invention but are not intended to limit the scope thereof in any way. Temperatures are given in degrees Centigrade and data regarding parts relate to parts by weight. Unless defined otherwise, the evaporation of solvents is carried out under reduced pressure, for example between approximately 0.1 and 15 mm Hg.

EXAMPLE 1

262 g of copper (II) acetoacetate are added slowly to a solution of 290 g of (+)-cyanidan-3-ol in 2 liters of anhydrous pyridine. After stirring for 10 minutes at room temperature, 242 g of diphenyldichloromethane are added in small portions. This mixture is stirred for 3 hours at room temperature and then the precipitate which forms if filtered off. The solvent is completely evaporated and the residue is dissolved in 1.5 liters of ether. This solution is washed 4 times with a solution made up of 80 g of EDTA in 2 liters of water; at each washing the solution is stirred for 1 hour. After drying on magnesium sulphate and evaporation of the ether, the resulting oily residue is washed in acetone until solidification. The solid is filtered off and added to 500 ml of chloroform, and the suspension is stirred for 1 hour then filtered. The precipitate is recrystallised in a mixture of methyl alcohol and water. After drying at 90° C. in vacuo, 3',4'-O,O-(diphenylmethylene)-(+)-cyanidan-3-ol is obtained. m.p.=216°–217° C.

EXAMPLE 2

A suspension of 4.5 g of finely divided potassium hydroxide in 15 ml of dimethylsulphoxide is prepared while stirring vigorously under nitrogen at room temperature. To this suspension are added simultaneously 3.08 g of (+)-cyanidan-3-ol in 10 ml of dimethylsulphoxide and 2.6 g of dichlorodiphenylmethane in 5 ml of dimethylsulphoxide. The solution rapidly becomes dark and stirring is maintained for 3 hours at a temperature not rising above 35° C. The mixture is then poured onto stirred crushed ice, the solution is neutralised to pH7 with a 10% aqueous solution of sulphuric acid, then extracted with ethyl acetate. The organic layer is washed several times with water before evaporation of the solvent. The solid residue is crystallized in a mixture of methanol and water. 3',4'-O,O-(diphenylmethylene)-(+)-cyanidan-3-ol is obtained. m.p.=216°–217° C.

EXAMPLE 3

4.5 g of 3',4'-O,O-(diphenylmethylene)-(+)-cyanidan-3-ol are dissolved in 60 ml of dry pyridine and stirred, then 4.9 g of benzoyl chloride are added dropwise. One hour after the addition of the reagents, the solution is poured onto crushed ice while stirring vigorously, the precipitated compound is filtered and washed with an aqueous sodium bicarbonate solution, then with water. This product is dried and crystallised in a mixture of acetone and hexane. In this way, 3,5,7-tri-O-benzoyl-3',4'-O,O-(diphenylmethylene)-(+)-cyanidan-3-ol is obtained. m.p.=163°–164° C.

EXAMPLE 4

9 g of 3',4'-O,O-(diphenylmethylene)-(+)-cyanidan-3-ol dissolved in 100 ml of dimethylformamide are added dropwise to a stirred mixture of 3.5 g of sodium hydride dispersion in paraffin oil (containing 55% by weight of sodium hydride) in 40 ml of dry dimethylformamide. The reaction mixture is cooled to −5° C. and stirring is continued for 30 minutes after the addition has been completed. Subsequently 14 g of methyl iodide dissolved in 30 ml of dimethylformamide are added dropwise. The mixture is stirred for one hour at room temperature. The precipitate is removed by filtration and washed with chloroform. The filtrate is evaporated in vacuo and the remaining residue is dissolved in chloroform. The combined chloroform solutions are washed with water and dried on magnesium sulphate. The solution is heated under reflux with activated charcoal for half an hour. After filtration and evaporation of the solvent, the residue is dried in vacuo. 3,5,7-tri-O-methyl-3',4'-O,O-(diphenylmethylene)-(+)-cyanidan-3-ol are obtained as a white solid. m.p.=138°–139° C.

EXAMPLE 5

5 g of 3',4'-O,O-(diphenylmethylene)-(+)-cyanidan-3-ol are dissolved in 25 ml of pyridine, and 25 ml of acetic anhydride are then added. The solution is stirred at room temperature for 16 hours and poured into 500 ml of ice-water. On stirring the resulting mixture for a period of 2 hours, a solid is formed. It is filtered, washed with water, dried and then crystallised from a mixture of isopropanol and water to give 3,5,7-tri-O-acetyl-3',4'-O,O-(diphenylmethylene)-(+)-cyanidan-3-ol. m.p.=139°–140° C.

EXAMPLE 6

29.0 g of (+)-cyanidan-3-ol are dissolved in 200 ml of 1,2-dimethoxyethane under a nitrogen atmosphere. To this solution, 16.0 g of pyridine are added followed by 20.0 g of cupric acetate monohydrate. The mixture is stirred for 15 minutes and then 32.5 g dichloro-di-(4-fluorophenyl)-methane are added over a period of 30 minutes at such a rate that a temperature of 20°–25° C. is maintained throughout. Upon completion of the addition, stirring is continued for a further 3 hour at 20°–25° C. After this time, the copper salts are filtered and the filtrate is evaporated in vacuo to give a dark brown oil. 400 ml of diethyl ether are immediately added and the insoluble impurities are removed by filtration. The ether solution is washed with a solution of sodium bicarbonate in water followed by a solution of ethylenediaminetetraacetic acid in water and then dried over magnesium sulphate and evaporated. The residual brown oil is made into a slurry with carbon tetrachloride and then filtered. The crude product is dissolved in acetone, a seed crystal is added and the solution is cooled to 0° C. and left at this temperature for 2 days. The crystallised material is filtered and dried in vacuo to give 3',4'-O,O-[di-(4''-fluorophenyl)-methylene]-(+)-cyanidan-3-ol. m.p.: 110°–111° C.

EXAMPLE 7

As in Example 6 using a solution of 25.0 g of 9,9-dichlorofluorene in 100 ml of 1,2-dimethoxyethane. The crude material is filtered and allowed to dry to give a yellow-brown solid which is crystallised from a mixture of chloroform and methanol. After filtration of the precipitated solid and drying in air, distilled water is added. Approximately half the volume of water is removed by evaporation and the resulting slurry is then filtered. The purified material is dried in vacuo over phosphorous pentoxide to give 3',4'-O,O-(9'',9''-fluorenylidene)-(+)-cyanidan-3-ol. m.p.: >300° C.

EXAMPLE 8

As in Example 6 using a solution of 49.5 g of dichloro-di-(4-acetoxyphenyl)-methane in 40 ml of 1,2 dimethoxyethane. Elution of the resulting brown solid on a silica gel column with a mixture of chloroform and methanol at a 70 p.s.i. pressure yields 3',4'-O,O-[di-(4''-acetoxyphenyl)methylene]-(+)-cyanidan-3-ol. m.p.: 129°–132° C.

EXAMPLE 9

As in Example 6 using a solution of 32.0 g of dichloro-(4-nitrophenyl)phenylmethane in 100 ml of 1,2-dimethoxyethane. Elution of the resulting brown solid on a silica gel column with a mixture of cyclohexane and diethyl ether at a 40 p.s.i pressure yields 3',4'-O,O-[(4''-nitrophenyl)-phenylmethylene]-(+)-cyanidan-3-ol. m.p.: 99°–100° C.

EXAMPLE 10

22.7 g of 3',4'-O,O-(diphenylmethylene)-(+)-cyanidan-3-ol are dissolved in 150 ml of triethylamine and a solution of 17.5 g of succinic anhydride in 150 ml of pyridine is then added. The solution is stirred at 50° C. for 1 hour and a half and the solvents are evaporated. The residue is dissolved in ethyl acetate and extracted with a 10% aqueous sodium carbonate solution, the aqueous layer is separated, acidified with hydrochloric acid and extracted in turn with ethyl acetate. After evaporation of the organic phase, the compound is purified by elution through a dry silica gel Woelm AIII column with a mixture of dichloromethane and ethyl acetate. 3-O-(3-carboxypropionyl)-3',4'-O,O-(diphenylmethylene)-(+)-cyanidan-3-ol is obtained. m.p.: 110°–111° C.

EXAMPLE 11

4.7 g of 3-(3-carboxypropionyl)-3',4'-O,O-(diphenylmethylene)-(+)-cyanidan-3-ol are treated in 100 ml of water containing 715 mg of sodium bicarbonate and stirred until there is complete dissolution. After filtration and freeze drying of the solution the sodium salt of 3-O-(3-carboxypropionyl)-3',4'-O,O-(diphenylmethylene)-(+)-cyanidan-3-ol is obtained.

EXAMPLE 12

As in example 6 using a solution of 34.0 g of dichloro-(4-ethoxycarbonylphenyl)phenylmethane in 100 ml of 1,2-dimethoxyethane. Elution of the resulting brown solid on a silica gel column with a mixture of chloroform and methanol at 70 p.s.i pressure yields 3',4'-O,O-[(4''-ethoxycarbonylphenyl)-phenyl-methylene]-(+)-cyanidan-3-ol.

EXAMPLE 13

As in example 8, when the resulting material is submitted to slight acidic conditions in a mixture of methanol and water. The precipitate obtained after adding sufficient water is thoroughly washed with water then dried to yield 3',4'-O,O-[di-(4''-hydroxyphenyl)-methylene]-(+)-cyanidan-3-ol.

EXAMPLE 14

A suspension of 138 g anhydrous potassium carbonate in 200 ml diethylketone is prepared while stirring vigorously under nitrogen at room temperature. To this suspension is added a solution of 29,0 g (+)-cyanidan-3-ol in 300 ml dimethylformamide, then the temperature is raised to 100° C. and 69,9 g methylene bromide is added dropwise. Stirring is maintained for 2 hours at 100° C. After cooling the mixture, the potassium carbonate is filtered and washed with dimethylformamide. The mixed filtrates are diluted with water and extracted with ethyl acetate. The ethyl acetate solution is in turn washed with water, then evaporated. The residue is eluted on a dry silicagel column with a mixture of ethanol and methylene chloride. One obtains 3',4'-O,O-(methylene)-(+)-cyanidan-3-ol. m.p. 113° C.:

EXAMPLE 15

A solution of 29 g (+)-cyanidan-3-ol in 670 ml pyridine is prepared under nitrogen at 40° C. 110 g anhydrous potassium carbonate are added, followed by 36,8 g dichlorodiphenylmethane. The resulting mixture is stirred efficiently and held at 40° C. for 9 hours. After cooling to room temperature one liter water is added and the crude product extracted with chloroform. The organic extract is washed with 5M hydrochloric acid and water, then dried and evaporated in vacuo. The residue is dissolved in 300 ml acetone and stirred until a fine precipitate is formed, then this suspension is cooled to −10° C. and allowed to stand overnight. The crude product is filtered, suspended into 120 ml acetone and heated at reflux for 30 minutes. After cooling to room temperature overnight, the solid is filtered and washed with acetone. The damp material is purified by crystallisation twice from a mixture of methanol and water. 200 ml distilled water are then added to the purified product and half the volume of water is evaporated at atmospheric pressure. The solid is filtered and dried at 50° C. to give 3',4'-O,O-diphenylmethylene-(+)-cyanidan-3-ol. m.p. 216°-217° C.

EXAMPLE 16

As in example 15 using 110 ml triethylamine and adding 25 ml water instead of 110 g anhydrous potassium carbonate. The damp material obtained after acetone treatment is crystallised twice from methanol instead of a mixture of methanol and water, then 300 ml distilled water are added to the purified product and approximately 75 ml water are evaporated off at atmospheric pressure over 4 hours. After cooling to room temperature the solid is filtered and dried at 50° C. to give 3',4'-O,O-diphenylmethylene-(+)-cyanidan-3-ol. m.p. 216°-217° C.

EXAMPLE 17

As in example 15 using 650 ml acetonitrile, 150 ml pyridine instead of 670 ml pyridine and 81 g N-methylmorpholine instead of 110 g anhydrous potassium carbonate. One obtains 3',4'-diphenylmethylene-(+)-cyanidan-3-ol. m.p. 216°-217° C.

EXAMPLE 18

As in example 15 using 650 ml isopropanol, 150 ml pyridine instead of 670 ml pyridine and 92,8 g N,N,N',N'-tetramethylethylenediamine instead of 110 g anhydrous potassium carbonate. The damp material obtained after acetone treatment is crystallised from methanol instead of a mixture of methanol and water, then 500 ml distilled water are added to the purified product and approximately 200 ml water are evaporated at atmospheric pressure over 4 hours. The resulting suspension is cooled to ambient temperature, the solid is filtered and dried at 50° C. to give 3',3'-O,O-diphenylmethylene-(+)-cyanidan-3-ol. m.p. 216°-217° C.

EXAMPLE 19

As in example 17 using 81 g diisopropylamine instead of N-methylmorpholine. One obtains 3',4'-O,O-diphenylmethylene-(+)-cyanidan-3-ol. m.p. 216°-217° C.

EXAMPLE 20

As in example 1 using 200 g of copper (II) acetate monohydrate instead of 262 g of copper (II) acetoacetate. One obtains 3',4'-O,O-diphenylmethylene-(+)-cyanidan-3-ol. m.p. 216°-217° C.

We claim:

1. A compound of the formula

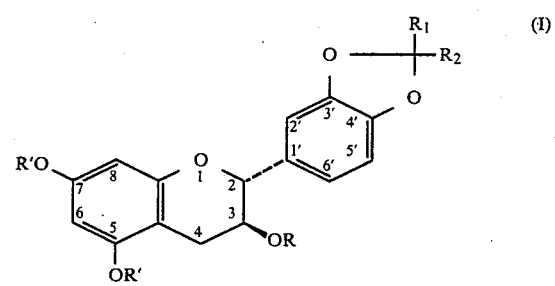

wherein
R and R' independently represent hydrogen; lower alkyl which is unsubstituted or substituted by hydroxy, oxo, amino, imino, di-lower alkylamino, halo, hydroxyimino, phenylimino, nitrophenylimino, acetylimino, cyano, carboxy or lower alkylsulfinyl; lower alkenyl which is unsubstituted or substituted by carboxy, lower alkylcarboxy, nitro, methylsulfinyl or acetoxymethylthio; lower alkynyl; cycloalkyl-lower alkyl wherein cycloalkyl has 3 to 6 ring carbon atoms; cycloalkenyl-lower alkyl wherein cycloalkenyl has 5 to 6 carbon atoms; phenyl or phenyl-lower alkyl which are unsubstituted or substituted by halo, lower alkyl, lower alkoxy, nitro or di-lower alkylamino; carboxy substituted lower alkanoyl; lower alkenoyl; carboxy substituted lower alkenoyl; trifluoroacetyl; or benzoyl or benzoyl substituted by hydroxy, halo, lower alkyl or lower alkoxy;
$R_1$ and $R_2$ independently represent phenyl or phenyl substituted by hydroxy, halo, lower alkyl, lower alkoxy, nitro, lower alkoxycarbonyl, lower alkanoyloxy, or dimethylamino; or $R_1$ and $R_2$ together represent biphenyl-2,2'-ylene which is unsubstituted or substituted by hydroxy, halo, lower alkyl, lower alkoxy, nitro, lower alkoxycarbonyl, lower alkanoyloxy or dimethylamino, and therapeutically acceptable salts thereof.

2. A compound according to claim 1, wherein R and R' are hydrogen or lower alkylbenzyl, and $R_1$ and $R_2$ are phenyl or phenyl substituted by halo, nitro, lower alkoxy or lower alkanoyloxy, and therapeutically acceptable salts thereof.

3. A pharmaceutical composition for the treatment of liver or venous diseases containing an effective amount of a compound according to claim 1 and a pharmaceutical carrier.

4. A composition according to claim 3, wherein said compound is 3',4'-O,O-(diphenylmethylene)-(+)-cyanidan-3-ol.

5. A composition according to claim 3, wherein said compound is 3',4'-O,O-[di-(4''-fluorophenyl)-methylene]-(+)-cyanidan-3-ol.

6. A composition according to claim 3, wherein said compound is 3-(3-carboxypropionyl)-3',4'-O,O-(diphenylmethylene)-(+)-cyanidan-3-ol.

7. A method for the treatment of liver diseases, which comprises administering to a living body suffering from liver diseases an effective amount of a compound of formula I as claimed in claim 1.

8. A method for the treatment of venous diseases, which comprises administering to a living body suffering from venous diseases an effective amount of a compound of formula I as claimed in claim 1.

9. 3',4'-O,O-(diphenylmethylene)-(+)-cyanidan-3-ol.

10. 3',4-O,O[di-(4''-fluorophenyl)-methylene]-(+)-cyanidan-3-ol.

11. 3-(3-carboxypropionyl)-3',4'-O,O-(diphenylmethylene)-(+)-cyanidan-3-ol sodium salt.

* * * * *